United States Patent [19]

Heinemann et al.

[11] Patent Number: 4,965,265

[45] Date of Patent: Oct. 23, 1990

[54] FUNGICIDAL 4-AZA-1,10-PHENANTHROLINE DERIVATIVES

[75] Inventors: Ulrich Heinemann; Wilhelm Brandes, both of Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 336,925

[22] Filed: Apr. 12, 1989

[30] Foreign Application Priority Data

May 7, 1988 [DE] Fed. Rep. of Germany ....... 3815617

[51] Int. Cl.$^5$ ................... C07D 471/04; A01N 43/90; A01N 55/02; A01N 55/04
[52] U.S. Cl. ................................... 514/250; 544/225; 544/345
[58] Field of Search .......................... 544/345; 514/250

[56] References Cited

PUBLICATIONS

J. A. C. S., vol. 81, (1959), pp. 6297–6301.
Il'ina, Chem. Abs. 79, 32008f, (1973).
Pfeiffer, J. Org. Chem. 31, 3384, (1967).

*Primary Examiner*—Mark L. Berch
*Attorney, Agent, or Firm*—Spring Horn Kramer & Woods

[57] ABSTRACT

A fungicidal 4-aza-1,10-phenanthroline derivatives of the formula

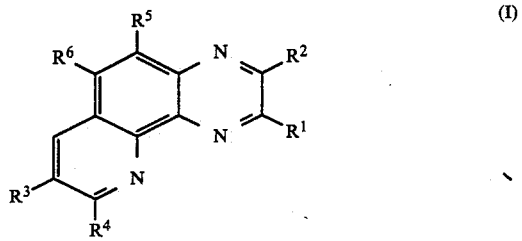

in which $R^1$ and $R^2$ are identical or different and stand for hydrogen, alkyl, optionally substituted aryl, optionally substituted hetaryl, or together with the carbon atoms to which they are bonded stand for a benzo group, $R^3$ and $R^4$ are identical or different and stand for hydrogen or alkyl and $R^5$ and $R^6$ individually stand for hydrogen or together with the carbon atoms to which they are bonded stand for a benzo group, with the exception of the compound 4-aza-1,10-phenanthroline, and addition products thereof with acids and metal salts.

10 Claims, No Drawings

FUNGICIDAL 4-AZA-1,10-PHENANTHROLINE DERIVATIVES

The present invention relates to new 4-aza-1,10-phenanthroline derivatives, to several processes for their preparation and to their use in pesticides, in particular as fungicides.

The synthesis of the unsubstituted 4-aza-1,10-phenanthroline and its property to form chelates with, for example, Fe(II) and if appropriate Cu(I) are known. (cf. J. A. C. S., 6297–6301, Vol. 81, 1959).

New 4-aza-1,10-phenanthroline derivatives of the formula (I)

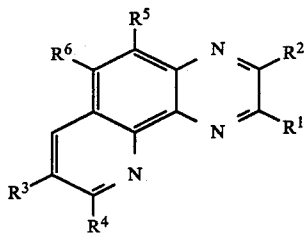

have now been found, in which
R¹ and R² are identical or different and stand for hydrogen, alkyl, optionally substituted aryl, optionally substituted hetaryl, or together with the carbon atoms to which they are bonded stand for a benzo group,
R³ and R⁴ are identical or different and stand for hydrogen or alkyl and
R⁵ and R⁶ individually stand for hydrogen or together with the carbon atoms to which they are bonded stand for a benzo group,
with the proviso that at least one of R¹, R², R³, R⁴, R⁵ and R⁶ is other than hydrogen and their acid addition salts and metal salt complexes.

Furthermore, it has been found that the new 4-aza-1,10-phenanthroline derivatives of the formula (I)

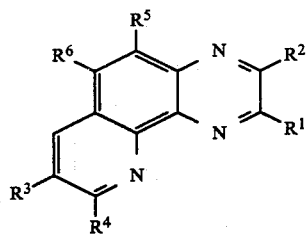

in which
R¹ and R² are identical or different and stand for hydrogen, alkyl, optionally substituted aryl, optionally substituted hetaryl, or together with the carbon atoms to which they are bonded stand for a benzo group,
R³ and R⁴ are identical or different and stand for hydrogen or alkyl and
R⁵ and R⁶ individually stand for hydrogen or together with the carbon atoms to which they are bonded stand for a benzo group,
with the proviso that at least one of R¹, R², R³, R⁴, R⁵ and R⁶ is other than hydrogen and their acid addition salts and metal salt complexes are obtained when
(A) 5-aminoquinoxalines of the formula (II)

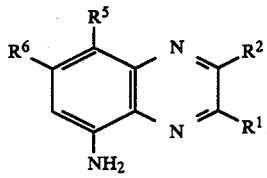

in which R¹, R², R⁵ and R⁶ have the abovementioned meanings, but where R¹, R², R⁵ and R⁶ do not simultaneously stand for hydrogen,
(α) are cyclized with aldehydes of the formula (III)

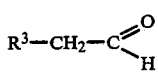

in which R³ has the abovementioned meaning, if appropriate in the presence of diluents and if appropriate in the presence of strong acids, in particular Lewis acids, and, if appropriate, the resultant products are converted into acid addition salts or metal salt complexes, or
(β) are cyclized with α,β-unsaturated aldehydes of the formula (IIIa)

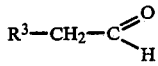

in which R³ and R⁴ have the abovementioned meanings, if appropriate in the presence of diluents and if appropriate in the presence of a strong acid or if appropriate in the presence of an oxidant or with the removal of water, if appropriate in the presence of a catalyst, and, if appropriate, the resultant products are converted into acid addition salts or metal salt complexes, or the 4-aza-1,10-phenanthroline derivatives of the formula (I) are obtained when
(B) 7,8-diaminoquinolines of the formula (IV)

in which R³ and R⁴ have the abovementioned meanings, are reacted with 1,2-diketones of the formula (V)

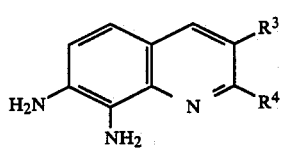

in which R¹ and R² have the abovementioned meanings, if appropriate in the presence of a diluent, and, if appropriate, the resultant products are converted into acid addition salts or metal salt complexes.

Moreover, it has been found that the new 4-aza-1,10-phenanthroline derivatives of the formula (I) and their acid addition salts and metal salt complexes are distinguished by powerful biological properties.

Surprisingly, the 4-aza-1,10-phenanthroline derivatives according to the invention of the formula (I) and their acid addition salts and metal salt complexes show a good action against pests, in particular fungi.

The 4-aza-1,10-phenanthroline derivatives according to the invention thus represent a valuable enrichment of the art.

Formula (I) provides a general definition of the 4-aza-1,10-phenanthroline derivatives according to the invention. Preferred compounds of the formula (I) are those in which $R^1$ and $R^2$ are identical or different and stand for hydrogen, straight-chain or branched alkyl having 1 to 4 carbon atoms; phenyl which is optionally monosubstituted to trisubstituted by identical or different substituents from the series comprising halogen, alkyl having 1 to 4 carbon atoms or alkoxy having 1 to 4 carbon atoms; a 5- or 6-ring hetaryl which has 1 or 2 identical or different hetero atoms, such as oxygen, sulphur or nitrogen, and which is optionally monosubstituted to trisubstituted by identical or different substituents from the series comprising halogen or alkyl having 1 to 4 carbon atoms, for example for pyridyl, pyrimidinyl or furanyl, or together with the carbon atoms to which they are bonded stand for a benzo group, $R^3$ and $R^4$ are identical or different and stand for hydrogen or straight-chain or branched alkyl having 1 to 4 carbon atoms and $R^5$ and $R^6$ individually stand for hydrogen or together with the carbon atoms to which they are bonded stand for a benzo group, with the proviso that at least one of $R^1$, $R^2$, $R^3$, $R^4$, $R^5$ and $R^6$ is other than hydrogen.

Particularly preferred compounds of the formula (I) are those in which $R^1$ and $R^2$ are identical or different and stand for hydrogen, methyl, ethyl, n- or i-propyl, n-, i-, s- or t-butyl; phenyl which is optionally monosubstituted or disubstituted by identical or different substituents from the series comprising fluorine, chlorine, bromine, methyl, ethyl, n- or i-propyl, methoxy and/or ethoxy; for pyridyl, pyrimidinyl or furanyl, each of which is optionally monosubstituted to trisubstituted by identical or different substituents from the series comprising fluorine, chlorine, bromine, methyl and/or ethyl, or together with the carbon atoms to which they are bonded stand for a benzo group, $R^3$ and $R^4$ are identical or different and stand for hydrogen, methyl, ethyl, n- or i-propyl, n-, i-, s- or t-butyl and $R^5$ and $R^6$ individually stand for hydrogen or together with the carbon atoms to which they are bonded stand for a benzo group, with the proviso that at least one of $R^1$, $R^2$, $R^3$, $R^4$, $R^5$ and $R^6$ is other than hydrogen.

Other preferred compounds according to the invention are addition products from acids and those 4-aza-1,10-phenanthroline derivatives of the formula (I) in which $R^1$, $R^2$, $R^3$, $R^4$, $R^5$ and $R^6$ have those meanings which have already been preferably mentioned for these substituents in connection with the description of the substances according to the invention.

The acids which can be added on preferably include hydrohalic acid, such as, for example, hydrochloric acid and hydrobromic acid, in particular hydrochloric acid, furthermore phosphoric acid, sulphuric acid, nitric acid, mono- and bifunctional carboxylic acids and hydroxycarboxylic acids, such as, for example, acetic acid maleic acid, succinic acid, fumaric acid, tartaric acid, citric acid, salicylic acid, sorbic acid and lactic acid, oleic acid, stearic acid, benzoic acid which is optionally monosubstituted to polysubstituted by nitro or halogen, gluconic acid, ascorbic acid, malic acid, sulphamic acid, sulfonic acids, such as, for example, p-toluenesulphonic acid, 1,5-naphthalinedisulphonic acid and methanesulphonic acid, and also imides, such as, for example, phthalimide, saccharin and thiosaccharin.

Other preferred compounds according to the invention are also addition products with salts of metals of main groups I, II and III and of tin, and furthermore salts of metals of sub-groups I, II, VII and VIII of the Periodic Table of the Elements and those 4-aza-1,10-phenanthroline derivatives of the formula (I) in which $R^1$, $R^2$, $R^3$, $R^4$, $R^5$ and $R^6$ have the meanings which have already been preferably mentioned for these substituents in connection with the description of the substances of the formula (I) according to the invention.

Here, the salts of copper, zinc, manganese, magnesium, calcium, tin, iron, cobalt and of nickel are particularly preferred. Suitable anions of these salts are those which are derived from those acids which lead to physiologically acceptable addition products. In this connection, acids of this type which are particularly preferred are the hydrohalic acids, such as, for example, hydrochloric acid and hydrobromic acid, furthermore phosphoric acid, nitric acid and sulphuric acid.

Besides the compounds mentioned in the Preparation Examples, the following 4-aza-1,10-phenanthroline derivatives of the general formula (I) may be mentioned individually:

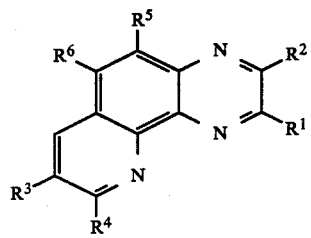

(I)

TABLE 1

| $R^1$ | $R^2$ | $R^3$ | $R^4$ | $R^5$ | $R^6$ |
|---|---|---|---|---|---|
| CH$_3$ | CH$_3$ | H | CH$_3$ | H | H |
| C$_2$H$_5$ | C$_2$H$_5$ | H | CH$_3$ | H | H |
| H | H | CH$_3$ | C$_2$H$_5$ | H | H |
| H | H | CH$_3$ | C$_2$H$_5$ | —CH=CH—CH=CH— | |
| | —CH=CH—CH=CH— | CH$_3$ | C$_2$H$_5$ | H | H |

TABLE 1-continued
| R¹ | R² | R³ | R⁴ | R⁵ | R⁶ |
|---|---|---|---|---|---|
| 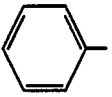 | H | H | CH₃ | —CH=CH—CH=CH— | |
| 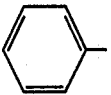 | H | H | CH₃ | H | H |
| C₂H₅ | CH₃ | H | CH₃ | H | H |
| n-C₃H₇— | n-C₃H₇— | H | CH₃ | H | H |
| n-C₃H₇— | CH₃ | CH₃ | C₂H₅ | H | H |
| —CH=CH—CH=CH— | | H | CH₃ | H | H |
| —CH=CH—CH=CH— | | H | CH₃ | —CH=CH—CH=CH— | |
| 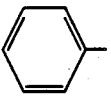 | 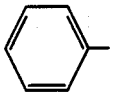 | CH₃ | C₂H₅ | H | H |
| 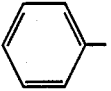 | 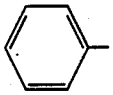 | H | CH₃ | H | H |
| H | H | C₂H₅ | n-C₃H₇— | H | H |
| H | H | i-C₃H₇— | s-C₄H₉ | H | H |
| CH₃ | CH₃ | C₂H₅ | n-C₃H₇ | H | H |
| C₂H₅ | C₂H₅ | CH₃ | C₂H₅ | H | H |
| —CH=CH—CH=CH— | | C₂H₅ | n-C₃H₇ | H | H |
| 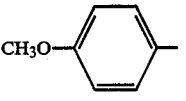 | 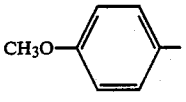 | CH₃ | C₂H₅ | H | H |
| 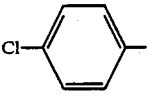 | 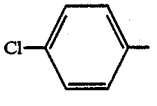 | CH₃ | C₂H₅ | H | H |
| 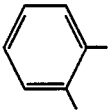 | 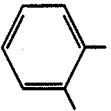 | H | CH₃ | H | H |
| 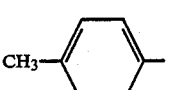 | 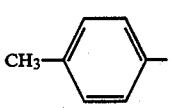 | H | CH₃ | H | H |
| 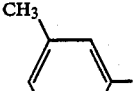 | 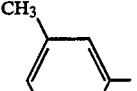 | CH₃ | C₂H₅ | H | H |
| 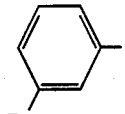 | 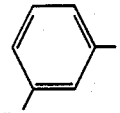 | CH₃ | C₂H₅ | H | H |

TABLE 1-continued
| R¹ | R² | R³ | R⁴ | R⁵ | R⁶ |
|---|---|---|---|---|---|
| 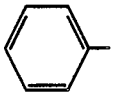 | CH₃ | CH₃ | C₂H₅ | H | H |
| 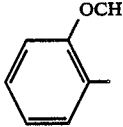 | 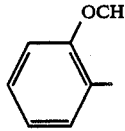 | H | CH₃ | —CH=CH—CH=CH | |
| 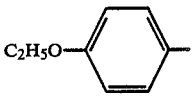 | H | H | CH₃ | —CH=CH—CH=CH | |
| 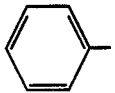 | CH₃ | C₂H₅ | n-C₃H₇— | H | H |
| 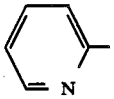 | 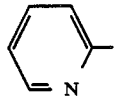 | CH₃ | C₂H₅ | H | H |
| 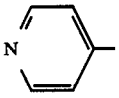 | 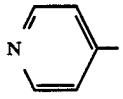 | CH₃ | C₂H₅ | H | H |
| 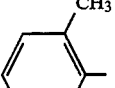 | 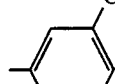 | H | CH₃ | H | H |
| 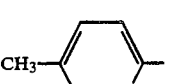 | 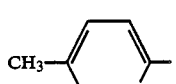 | CH₃ | C₂H₅ | H | H |
| 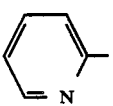 | 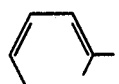 | H | CH₃ | —CH=CH—CH=CH | |
|  | 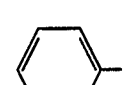 | CH₃ | C₂H₅ | H | H |
| 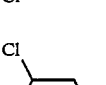 | 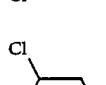 | CH₃ | C₂H₅ | H | H |

TABLE 1-continued
| R¹ | R² | R³ | R⁴ | R⁵ | R⁶ |
|---|---|---|---|---|---|
| 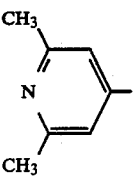 | 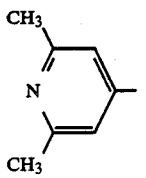 | CH₃ | C₂H₅ | H | H |
| 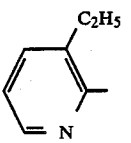 | 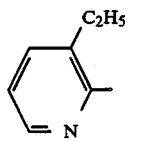 | H | CH₃ | H | H |
| 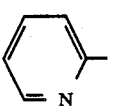 | H | CH₃ | C₂H₅ | H | H |
| 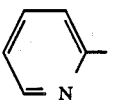 | H | H | CH₃ | H | H |
| 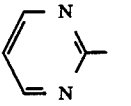 | 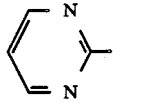 | CH₃ | C₂H₅ | H | H |
| 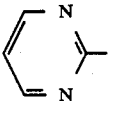 | 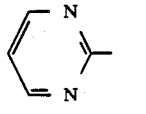 | H | CH₃ | H | H |
| 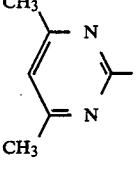 | 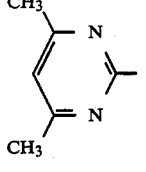 | H | CH₃ | —CH=CH—CH=CH— | |
| 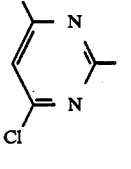 | 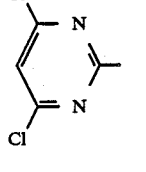 | CH₃ | C₂H₅ | H | H |
| 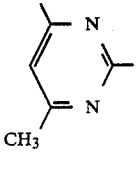 | 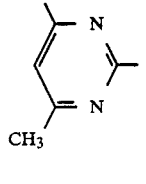 | CH₃ | C₂H₅ | H | H |
| 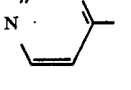 | 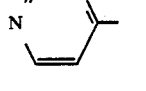 | CH₃ | C₂H₅ | H | H |

TABLE 1-continued
| R¹ | R² | R³ | R⁴ | R⁵ | R⁶ |
|---|---|---|---|---|---|
| 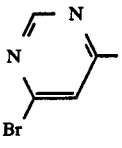 | 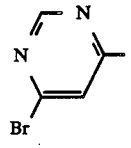 | H | CH₃ | H | H |
| 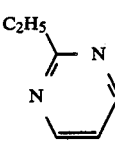 | 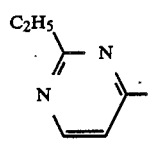 | CH₃ | C₂H₅ | H | H |
| 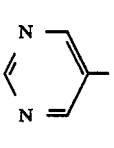 | 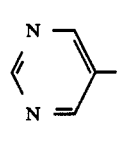 | C₂H₅ | n-C₃H₇ | H | H |
| 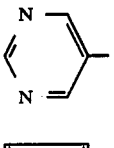 | H | CH₃ | C₂H₅ | H | H |
| 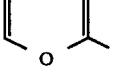 | 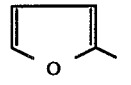 | CH₃ | C₂H₅ | H | H |
| 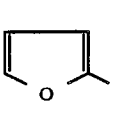 | 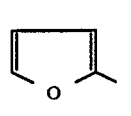 | H | CH₃ | H | H |
| 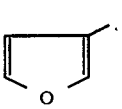 | 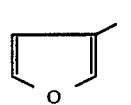 | CH₃ | C₂H₅ | H | H |
| 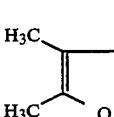 | 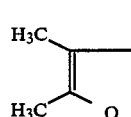 | H | CH₃ | H | H |
| 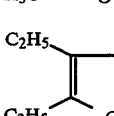 | 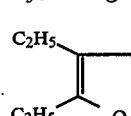 | CH₃ | C₂H₅ | H | H |
| 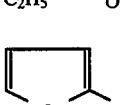 | 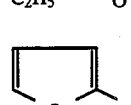 | H | CH₃ | —CH=CH—CH=CH |  |
| 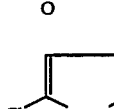 | 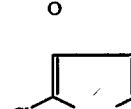 | CH₃ | C₂H₅ | H | H |
| 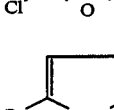 | 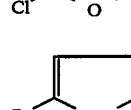 | CH₃ | C₂H₅ | H | H |
| 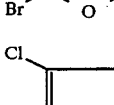 | 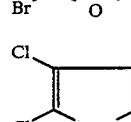 | H | CH₃ | H | H |
| 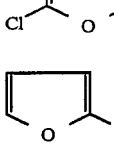 | H | CH₃ | C₂H₅ | H | H |

TABLE 1-continued

| R¹ | R² | R³ | R⁴ | R⁵ | R⁶ |
|---|---|---|---|---|---|
| 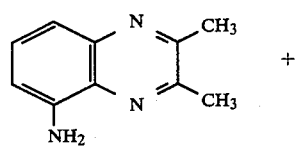 furan | H | H | $CH_3$ | H | H |
| 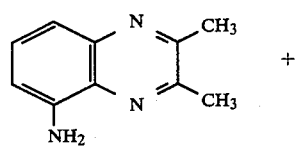 furan | H | H | $CH_3$ | —CH=CH—CH=CH— | |
| H₃C, CH₃ (dimethylfuran) H₃C | H | $CH_3$ | $C_2H_5$ | H | H |
| 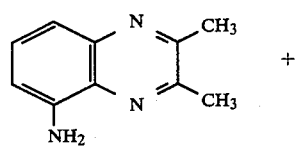 furan | $CH_3$ | $CH_3$ | $C_2H_5$ | H | H |
| 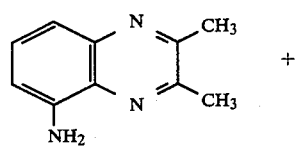 furan | $CH_3$ | H | $CH_3$ | H | H |
| 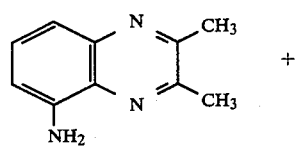 furan | $C_2H_5$ | H | $CH_3$ | H | H |

If, for example, 5-amino-2,3-dimethyl-quinoxaline and propionaldehyde are used as starting substances, the course of the reaction of preparation process (A/α) can be represented by the following equation:

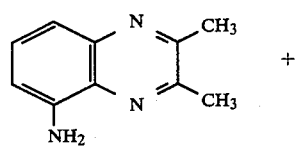

$$+ \quad 2 \times CH_3-CH_2-C\overset{O}{\underset{H}{\diagup}} \xrightarrow{AlCl_3}$$

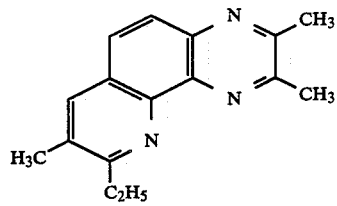

If, for example, 5-amino-2,3-dimethyl-quinoxaline and crotonaldehyde are used as starting substances, the course of the reaction of the preparation process (A/β) can be represented by the following equation:

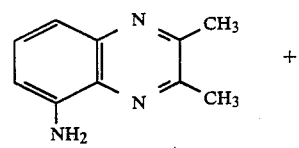

$$+ \quad CH_3-CH=CH-C\overset{O}{\underset{H}{\diagup}} \xrightarrow{H_2SO_4}$$

-continued

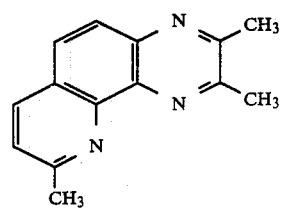

If, for example, 7,8-diaminoquinoline and diacetyl are used as starting substances, the course of the reaction of preparation process (B) can be represented by the following equation:

$$\begin{array}{c} CH_3-C=O \\ | \\ CH_3-C=O \end{array} \quad + \quad$$  $$\longrightarrow$$

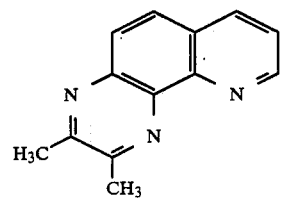

Formula (II) provides a general definition of the 5-aminoquinoxalines required as starting substances for carrying out process variants (A/α) and (A/β) according to the invention. In this formula (II), R¹, R², R⁵ and R⁶ preferably, or in particular, stand for those substituents which have been mentioned above as preferred, or particularly preferred, for these radicals in connection with the description of the new 4-aza-1,10-phenanthroline derivatives of the formula (I).

Some of the 5-aminoquinoxalines of the formula (II) are known and/or can be prepared by known processes in a simple, analogous manner (cf., for example, J. A. C. S 79, 2245–2248, (1957); J. Org. Chem. 31, 3384–3390, (1966) and Khim Geterotsikl. Soedin. 306–310 (1976)), for example by reducing the 5-nitroquinoxalines, some of which are likewise known, of the formula (VI)

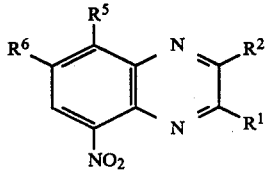
(VI)

in which $R^1$, $R^2$, $R^5$ and $R^6$ have the abovementioned meanings, if appropriate in the presence of a diluent in a customary manner and in the presence of a catalyst, such as, for example, Raney nickel or tin(II) salts, at temperatures between 20° C. and 150° C. and if appropriate under a pressure between 2 and 100 bar.

Some of the 5-nitroquinoxalines of the formula (VI) are known and/or can be prepared by known processes in a simple, analogous manner (cf. for example, J. Chem. Soc. 1953, 2822–2830), for example by (C) reacting o-phenylenediamines of the formula (VII)

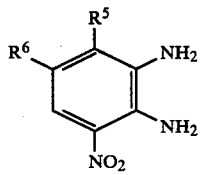
(VII)

in which $R^5$ and $R^6$ have the abovementioned meanings, with 1,2-diketones of the formula (V)

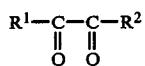
(V)

in which $R^1$ and $R^2$ have the abovementioned meanings, if appropriate in the presence of a diluent, such as, for example, water, acetic acid, methanol or ethanol, or mixtures of these solvents, at temperatures between 50° C. and 150° C., or the 5-nitroquinoxalines of the formula (VI) are obtained by (D) reacting o-benzoquinones of the formula (VIII)

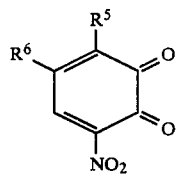
(VIII)

in which $R^5$ and $R^6$ have the abovementioned meanings, with ethylenediamine derivatives of the formula (IX)

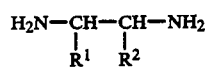
(IX)

in which $R^1$ and $R^2$ have the abovementioned meanings, if appropriate in the presence of a diluent, such as, for example, water, glacial acetic acid, methanol or ethanol, or mixtures of these solvents, at temperatures between 40° C. and 140° C.

The compounds of the formula (V), (VII), (VIII) and (IX) which are required as starting substances following processes (C) and (D) are generally known compounds of organic chemistry.

Formulae (III) and (IIIa) provide the general definitions of the aldehydes also to be used as starting substances for the preparation of the compounds of the formula (I) according to the invention according to processes (A/α) and (A/β). In formulae (III) and (IIIa), the radicals $R^3$ and $R^4$ preferably, or in particular, have the meaning which is mentioned above in connection with the description of the substances of the formula (I) according to the invention as being preferred.

The compounds of the formula (III) and (IIIa) are generally known compounds of organic chemistry.

Suitable diluents for carrying out the preparation process (A/α) and (A/β) are mixtures of strong inorganic or organic acids with water or inert organic solvents.

Examples of acids which can be used for carrying out the preparation process (A/α) or (A/β) are sulphuric acid, hydrochloric acid, p-toluenesulphonic acid and Lewis acids, such as, for example, aluminum chloride and iron(III) chloride, in particular aluminum chloride.

For carrying out preparation process (A/α), 1 mol of 5-aminoquinoxaline of the formula (II) is approximately reacted with an equimolar amount of a Lewis acid. An excess of one or the other reactant does not provide any substantial advantages.

Solvents which can be used for carrying out preparation process (A/α) or (A/β) are virtually all inert organic solvents, in particular aliphatic and aromatic, optionally halogenated hydrocarbons, such as, for example, benzine, benzene, toluene, xylene, chlorobenzene, dichlorobenzene, petroleum ether, pentane, hexane, heptane, ligroin or cyclohexane. Methylene chloride and chloroform are particularly preferred.

When carrying out preparation process (A/α) and (A/β), the reaction temperatures can be varied within a relatively wide range. In general, the processes are carried out at temperatures between 20° C. and 180° C., preferably at temperatures between 50° C. and 130° C.

Suitable oxidants for carrying out preparation process (A/β) are the oxidants which are customary for reactions of this type; arsenic acid or aromatic acids which contain nitro groups or their alkali metal salts, such as, for example, 3-nitrobenzenesulphonic acid, are preferably used.

For carrying out preparation processes (A/α) and (A/β), 1.0 to 4.0 moles, preferably 1.5 to 3.5 moles of aldehydes of the formula (III) or (IIIa) and if appropriate 1.0 to 2.0 moles, preferably 1.0 mole, of oxidant are employed per mole of 5-aminoquinoxaline of the formula (II). The reaction is carried out, and the reaction products of the formula (I) are worked up and isolated in a generally customary manner.

Formula (IV) provides a general definition of the 7,8-diaminoquinolines also to be used as the starting substances for the preparation of the compounds of the formula (I) according to the invention following process (B). In this formula (IV), the radicals $R^3$ and $R^4$ preferably, or in particular, have the meanings which are mentioned above in connection with the description of the substances of the formula (I) according to the invention as being preferred.

The compounds of the formula (IV) are generally known compounds of organic chemistry.

Formula (V) provides a general definition of the 1,2-diketones also to be used as starting substances for the preparation of the compounds of the formula (I) according to the invention following process (B). In this formula (V), the radicals $R^1$ and $R^2$ preferably, or in particular, have the meanings which are mentioned above in connection with the description of the substances according to the invention of the form (I) as being preferred.

The compounds of the formula (V) are generally known compounds of organic chemistry.

Suitable diluents for carrying out preparation process (B) are all inert solvents which are customary for reactions of this type. These preferably include water, glacial acetic acid, alcohols, such as methanol and ethanol, dimethylformamide or dimethyl sulphoxide, acetonitrile, ethers and also aliphatic and aromatic, optionally halogenated hydrocarbons, such as, for example, benzine, benzene, toluene, xylene, chlorobenzene, dichlorobenzene, petroleum ether, pentane, hexane, heptane, ligroin or cyclohexane. However, it is also possible to use mixtures of the mentioned diluents.

When carrying out preparation process (B), the reaction temperatures can be varied within a relatively wide range. In general, the process is carried out at temperatures between 20° C. and 180° C., preferably at temperatures between 60° C. and 140° C.

For carrying out preparation process (B), 1.0 to 3.0 moles, preferably 1.0 to 1.5 moles, of 1,2-diketones of the formula (V) are employed per mole of 7,8-diaminoquinoline of the formula (IV). The reaction product of the formula (I) is worked up and isolated by generally customary methods, such as, for example, by crystallization, filtering off with suction and drying.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and, if appropriate, purified by washing with an inert organic solvent.

Suitable metal salts for the preparation of metal salt complexes of the compounds of the general formula (I) are preferably those which have already been described further above.

The metal salt complexes of compounds of the general formula (I) can be obtained in a simple manner by customary processes, for example by dissolving the metal salt in alcohol, for example ethanol, and adding the mixture to compounds of the general formula (I). Metal salt complexes can be isolated in a known manner, for example by filtration, and, if appropriate, purified by recrystallization.

The active compounds according to the invention exhibit a powerful biological action and can be employed in practice for combating undesired pests. The active compounds can be employed, for example, for use as plant protection agents, mainly as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be employed with particularly good success protectively for combating Erysiphe species on barley, *Pyrenophora teres* on barley and Pyricularia species on rice.

It must be emphasised that the active compounds according to the invention can not only be employed protectively but also with particularly good success curatively for combating Phytophthora species on tomatoes.

Moreover, the active compounds according to the invention have a good action against Venturia species in apples and *Septoria nodorum* and *Cochliobolus sativus* on cereals and also in vitro.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable for example ligninsulphite waste liquors and methylcellulose.

Adhesives such as carboxymethylcellulose and natural and synthetic polymers in the form of powders, granules or lattices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The preparation and the use of the active compounds according to the invention can be seen from the examples below.

PREPARATION EXAMPLES

Example 1

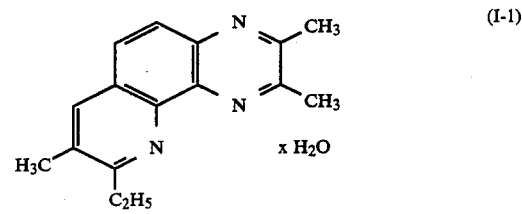

(Process (A/α), step 1)

9.3 g (0.160 mol) of propionaldehyde, dissolved in 50 ml of methylene chloride, are added dropwise at room temperature to a mixture of 13.3 g (0.076 mol) of 5-amino-2,3-dimethyl-quinoxaline and 10.2 g (0.076 mol) of aluminum chloride in 200 ml of dry methylene chloride and the mixture is then refluxed for 4 hours. After cooling, the solvent is removed by distillation under reduced pressure, the residue is taken up in water, the mixture is refluxed for 5 minutes and the hot mixture is then filtered. On cooling, crystals are formed from the filtrate which are filtered off with suction and dried.

3.2 g (16% of theory) of 9-ethyl-2,3,8-trimethyl-4-aza-1,10-phenanthroline are obtained as the monohydrate of melting point 137° C. to 138° C..

Example 2

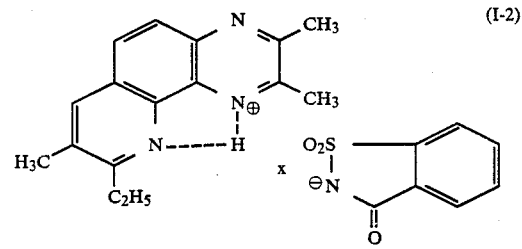

(Process A/α, step 2, salt formation)

1.6 g (0.006 mol) of 9-ethyl-2,3,8-trimethyl-4-aza-1,10-phenanthroline (Example 1) and 1.1 g (0.006 mol) of saccharin are refluxed for 5 minutes in 50 ml of dry methylene chloride. After cooling, the mixture is filtered, the filtrate is evaporated and the residue is stirred in ether, filtered off with suction and dried.

2.3 g (85% of theory) of the saccharin complex salt of 9-ethyl-2,3,8-trimethyl-4-aza-1,10-phenanthroline of melting point 198° C. to 200° C. are obtained.

Example 3

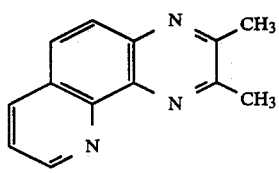
(I-3)

(Process B)

4.4 g (0.027 mol) of 7,8-diaminoquinoline and 2.6 g (0.030 mol) of diacetyl are refluxed for 1 hour in 100 ml of 10% strength acetic acid. After cooling to room temperature, the reaction mixture is diluted with 500 ml of water, rendered alkaline using concentrated sodium hydroxide solution and stored overnight in a refrigerator. The precipitated crystals are filtered off with suction, washed with a little cold water and dried.

2.1 g (37% of theory) of 2,3-dimethyl-4-aza-1,10phenanthroline of melting point 159° C. to 162° C. are obtained.

The end products of the formula (I)

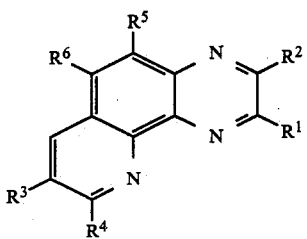
(I)

which are listed in Table 2 below are obtained in an analogous manner to the methods described in Examples 1 to 3 and with consideration of the instructions in the descriptions of the processes according to the invention:

TABLE 2

| Example No. | $R^1$ | $R^2$ | $R^3$ | $R^4$ | $R^5$ | $R^6$ | Metal complex Acid addition salt | Melting point (°C.) |
|---|---|---|---|---|---|---|---|---|
| I-4* | $C_2H_5/CH_3$ | $CH_3/C_2H_5$ | $CH_3$ | $C_2H_5$ | H | H | | 100–104 |
| I-5** | phenyl | H | $CH_3$ | $C_2H_5$ | H | H | | $^1$H-NMR δ = 7.15, 7.5; 1.55, 3.25; 2.6 |
| I-6 | —CH=CH—CH=CH— | | $CH_3$ | $C_2H_5$ | —CH=CH—CH=CH— | | | 172–175 |
| I-7* | $CH_3/C_2H_5$ | $C_2H_5/CH_3$ | $CH_3$ | $C_2H_5$ | H | H | $ZnCl_2$ | 238–250 |
| I-8 | $CH_3$ | $CH_3$ | H | $CH_3$ | H | H | | 185–188 |
| I-9 | $CH_3$ | $CH_3$ | $C_2H_5$ | H | H | H | | 149–153 |
| I-10 | $CH_3$ | $CH_3$ | H | $CH_3$ | H | H | | >300 |
| I-11 | $CH_3$ | $CH_3$ | H | $CH_3$ | H | H | $CuCl_2$ | 208–210 |
| I-12 | $CH_3$ | $CH_3$ | H | $CH_3$ | H | H | saccharate × 0.5 ethanol | 204–207 |
| I-13 | $CH_3$ | $CH_3$ | H | $CH_3$ | H | H | naphthalene-1,5-disulphonate | 280 (decompos.) |
| I-14 | $CH_3$ | $CH_3$ | $C_2H_5$ | H | H | H | $CuCl_2$ | 240 (decompos.) |
| I-15 | $CH_3$ | $CH_3$ | $C_2H_5$ | H | H | H | $ZnCl_2$ | >300 |
| I-16 | $CH_3$ | $CH_3$ | $C_2H_5$ | H | H | H | citrate | 142–147 |
| I-17 | $C_2H_5$ | $C_2H_5$ | H | $CH_3$ | H | H | | 155–157 |
| I-18 | $C_2H_5$ | $C_2H_5$ | $C_2H_5$ | H | H | H | | 85–87 |
| I-19 | 2-pyridyl | 2-pyridyl | H | $CH_3$ | H | H | ½$H_2O$ | 195–197 |
| I-20 | $C_2H_5$ | $C_2H_5$ | H | $CH_3$ | H | H | $ZnCl_2$ | 273–279 |
| I-21 | $C_2H_5$ | $C_2H_5$ | $C_2H_5$ | H | H | H | $ZnCl_2$ | 305–308 |
| I-22 | $C_2H_5$ | $C_2H_5$ | H | $CH_3$ | H | H | saccharate | 103–105 |
| I-23 | $C_2H_5$ | $C_2H_5$ | $CH_3$ | $C_2H_5$ | H | H | | 131–133 |
| I-24 | phenyl | phenyl | H | $CH_3$ | H | H | $H_2O$ | 219–221 |
| I-25 | phenyl | phenyl | H | $CH_3$ | H | H | $CuCl_2$ × ½$H_2O$ | 200 (decompos.) |

TABLE 2-continued

| Example No. | R¹ | R² | R³ | R⁴ | R⁵ | R⁶ | Metal complex Acid addition salt | Melting point (°C.) |
|---|---|---|---|---|---|---|---|---|
| I-26 | 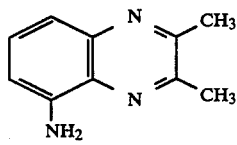 | H | H | CH₃ | H | H | | ¹H-NMR δ = 2,95 (s, 3H) |

*Compound (I-4) and (I-7) are present as isomer mixtures (position isomers).
**The ¹H-NMR-sprectra were recorded in deuterochloroform (CDCl₃) with tetramethylsilane (TMS) as the internal standard. The chemical shift is indicated as δ value in ppm.

Preparation of the Starting Substances

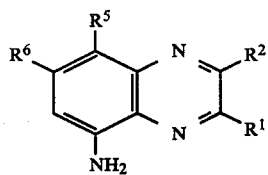 (II-1)

27.8 g (0.136 mol) of 2,3-dimethyl-5-nitro-quinoxaline are added in portions to 106.0 g (0.470 mol) of tin(II) chloride dihydrate in 300 ml of concentrated hydrochloric acid. During this process, the temperature rises to 50° C., and the reaction mixture is maintained at 50° C. for 1 hour. After cooling, the solids are filtered off with suction, the filter cake is suspended in 100 ml of concentrated sodium hydroxide solution, 100 ml of water are added, and the mixture is then stirred for approximately 30 minutes. The solids are subsequently filtered off with suction, and the filter cake is dissolved in 150 ml of methylene chloride. The organic phase is dried using sodium sulphate, the solvent is removed by distillation under reduced pressure and the residue is taken up in petroleum ether, filtered off with suction and dried.

18.6 g (79% of theory) of 5-amino-2,3-dimethyl-quinoxaline of melting point 162° C. to 163° C. are obtained.

The intermediates of the formula (II)

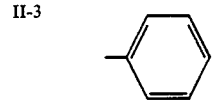 (II)

which are listed subsequently in Table 3 are obtained in an analogous manner to the process described in Example (II-1) and with consideration of the instructions in the descriptions of the processes.

TABLE 3

| Example No. | R¹ | R² | R⁵ | R⁶ | Melting point (°C.) |
|---|---|---|---|---|---|
| II-2* | CH₃/C₂H₅ | C₂H₅/CH₃ | H | H | 91–94 |
| II-3 | 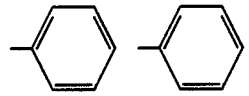 | H | H | H | 88–90 |
| II-4 | 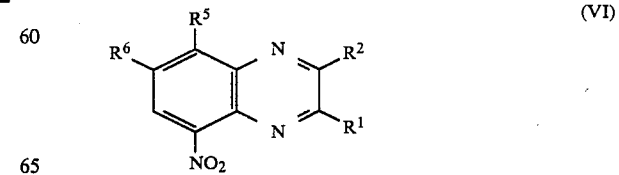 | | H | H | 242–245 |

TABLE 3-continued

| Example No. | R¹ | R² | R⁵ | R⁶ | Melting point (°C.) |
|---|---|---|---|---|---|
| II-5 | ![pyridyl] | ![pyridyl] | H | H | 110 (decompos.) |
| II-6 | C₂H₅ | C₂H₅ | H | H | 68–70 |
| II-7 | H— | ![furyl] | H | H | 145–146 |
| II-8** | ![furyl] | ![furyl] | H | H | ¹H-NMR δ = 6,5–6,6 |

*Compound (II-2) is present as an isomer mixture.
**The ¹H-NMR spectra were recorded in deuterochloroform (CDCl₃) with tetramethylsilane (TMS) as the internal standard. The chemical shift is indicated as δ value in ppm.

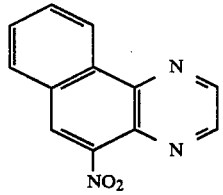 (VI-1)

20.3 g (0.10 mol) of 3-nitro-o-naphthoquinone and 6.0 g (0.10 mol) of ethylenediamine are stirred for 2 hours at 100° C. in 150 ml of glacial acetic acid. After cooling to room temperature, the reaction mixture is poured into 500 ml of water, and the precipitated precipitate is filtered off with suction, washed with water and dried. The residue is purified by chromatography over 100 g of aluminum oxide (eluant methylene chloride).

3.5 g (16% of theory) of 5-nitro-1,4-phenanthroline of melting point 163° C.–165° C. are obtained.

The intermediates of the formula (VI)

(VI)

which are listed subsequently in Table 4 are obtained in which an analogous manner to the process described in Example (VI-1) and with consideration of the instructions in the descriptions of the processes:

TABLE 4

| Example No. | R$^1$ | R$^2$ | R$^5$ | R$^6$ | Melting point (°C.) |
|---|---|---|---|---|---|
| VI-2 | CH$_3$ | CH$_3$ | H | H | 132–134 |
| VI-3* | CH$_3$/C$_2$H$_5$ | C$_2$H$_5$/CH$_3$ | H | H | 91–94 |
| VI-4 | phenyl | H | H | H | 170–171 |
| VI-5 | phenyl | phenyl | H | H | 168–171 |
| VI-6 | pyridyl | pyridyl | H | H | 198–200 |
| VI-7 | C$_2$H$_5$ | C$_2$H$_5$ | H | H | 97–100 |
| VI-8 | furyl | furyl | H | H | 117–120 |

*The compound (VI-3) is present as isomer mixture.

USE EXAMPLES

Example A

*Pyrenophora teres* test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, for example the substance (1-2) according to the invention shows a degree of effectiveness of 100% compared with the untreated control at a concentration of active compound of 0.025% by weight in the spray liquor.

Example B

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f. sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, for example the substance (I-2) according to the invention shows a degree of effectiveness of 88% compared with the untreated control at a concentration of active compound of 0.025% by weight in the spray liquor.

Example C

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, for example the substances (I-1), (I-2), (I-3), (I-4), (I-5) and (I-7) according to the invention show a degree of effectiveness of 100% compared with the untreated control at a concentration of active compound of 0.025%.

Example D

Phytophthora Test (tomato)/curative
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans*. The plants remain in an incubation cabin at 20° C. and 100% relative atmospheric humidity for 7 hours. After a short drying off time, the plants are sprayed with the preparation of active compound until dripping wet.

The plants are placed in an incubation cabin at 100% relative atmospheric humidity and at about 20° C.

Evaluation is carried out 3 days after the inoculation.

In this test, for example the compound (I-1) according to the invention shows a degree of effectiveness of nearly 90% at a concentration of active compound of 50 ppm.

It is understood that the specification and examples are illustrative but not limitative of the present invention and that other embodiments within the spirit and scope of the invention will suggest themselves to those skilled in the art.

We claim:

1. A 4-aza-1,10-phenanthroline or acid addition product thereof of the formula

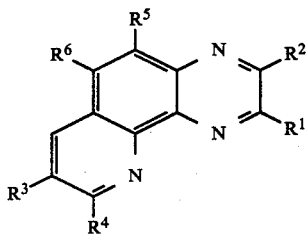

in which
R¹ and R² are identical or different and stand for hydrogen; or straight-chain or branched alkyl having 1 to 4 carbon atoms;
R³ and R⁴ are identical or different and stand for hydrogen or straight-chain or branched alkyl having 1 to 4 carbon atoms, and
R⁵ and R⁶ individually stand for hydrogen or together with the carbon atoms to which they are bonded stand for a benzo group,
with the exception of the compound 4-aza-1,10-phenanthroline 2. A fungicidal composition comprising a fungicidally effective amount of a compound or addition product thereof according to claim 1 and a diluent.

3. A 4-aza-1,10-phenanthroline according to claim 1, in which
R¹ and R² are identical or different and stand for hydrogen; or straight-chain or branched alkyl having 1 to 4 carbon atoms;
R³ and R⁴ are identical or different and stand for hydrogen or for straight-chain or branched alkyl having 1 to 4 carbon atoms and
R⁵ and R⁶ individually stand for hydrogen or together with the carbon atoms to which they are bonded stand for a benzo group,
with the exception of the compound 4-aza-1,10-phenanthroline.

4. A 4-aza-1,10-phenanthroline according to claim 1, which
R¹ and R² are identical or different and stand for hydrogen, methyl, ethyl, n- or i-propyl, n-, i-, s- or t-butyl;
R³ and R⁴ are identical or different and stand for hydrogen, methyl, ethyl, n- or i-propyl, n-, i-, s- or t-butyl and
R⁵ and R⁶ individually stand for hydrogen or together with the carbon atoms to which they are bonded stand for a benzo group,
with the exception of the compound 4-aza-1,10-phenanthroline.

5. A compound according to claim 1, wherein such compound is 9-ethyl-2,3,8-trimethyl-4-aza-1,10-phenanthroline of the formula

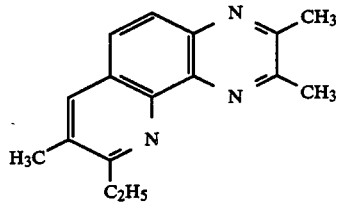

or an acid addition product thereof.

6. A mixture of compounds according to claim 1, wherein such compounds are 2,9-diethyl-3,8-dimethyl-4-aza-1,10-phenanthroline of the formula

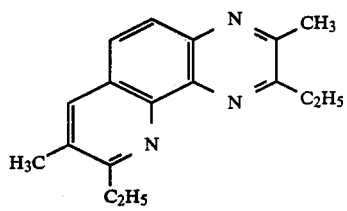

and 3,9-diethyl-2,8-dimethyl-4-aza-1,10-phenanthroline of the formula

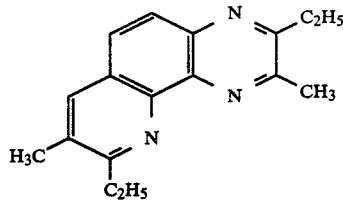

or acid addition products thereof.

7. A compound according to claim 1, wherein such compound is 2,3-diethyl-9-methyl-4-aza-1,10-phenanthroline of the formula

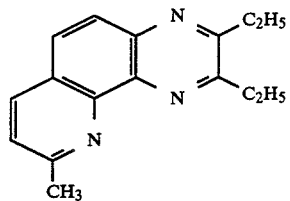

or an acid addition product thereof.

8. A compound according to claim 1, wherein such compound is 2,3,8-triethyl-4-aza-1,10-phenanthroline of the formula

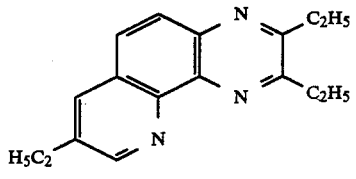

or an acid addition product thereof.

9. A method of combating fungi which comprises applying to such fungi a fungicidally effective amount of a 4-aza-1,10-phenanthroline or acid addition product thereof according to claim 1.

10. The method according to claim 9, wherein such compound is
9-ethyl-2,3,8-trimethyl-4-aza-1,10-phenanthroline,
2,9-diethyl-3,8-dimethyl-4-aza-1,10-phenanthroline, and
3,9-diethyl-2,8-dimethyl-aza-1,10-phenanthroline,
2,3-diethyl-9-methyl-4-aza-1,10-phenanthroline or
2,3,8-triethyl-4-aza-1,10-phenanthroline,
or an addition product thereof.

* * * * *